United States Patent [19]

Drinkwine et al.

[11] Patent Number: 5,789,258
[45] Date of Patent: Aug. 4, 1998

[54] METHOD FOR GENERATING VAPOR STREAMS

[75] Inventors: Arbor D. Drinkwine, Kansas City, Mo.; Brian R. Cage, Shawnee, Kans.

[73] Assignee: Midwest Research Institute, Kansas City, Mo.

[21] Appl. No.: 712,581

[22] Filed: Jun. 10, 1991

[51] Int. Cl.$^6$ ............................................. G01N 1/00
[52] U.S. Cl. ....................... 436/174; 136/147; 136/167; 136/181; 422/88; 422/93
[58] Field of Search ................... 73/1 G, 23.2, 23.35, 73/23.22; 422/88, 89, 93, 83; 436/167, 147, 181, 155, 109, 174

[56] References Cited

U.S. PATENT DOCUMENTS

| | | | |
|---|---|---|---|
| 2,880,071 | 3/1959 | Gelman | 422/93 |
| 3,459,938 | 8/1969 | Stenger et al. | 436/155 |
| 3,877,875 | 4/1975 | Jones et al. | 436/109 |
| 4,198,208 | 4/1980 | Lerner et al. | 436/155 |
| 4,942,018 | 7/1990 | Hunk | 422/70 |
| 5,089,232 | 2/1992 | May | 422/83 |

OTHER PUBLICATIONS

Pella, P., "Generator for Producting Trace Vapor Concentrations . . .", *Analytical Chemistry*, 48:1632–1637 (1976).

*Primary Examiner*—Lien Tran
*Attorney, Agent, or Firm*—Shook, Hardy & Bacon L.L.P.

[57] ABSTRACT

A method is provided for use in generating a chemical vapor stream which may be used to calibrate vapor detectors and for other purposes. The vapor generator is provided with a column having a temperature controlled zone. The chemical is coated onto a carrier such as glass beads and is placed in a temperature controlled zone. A carrier gas is passed over the chemical at a rate which permits the concentration of chemical vapors in the carrier gas to be at saturation. The exiting carrier gas contains chemical vapors at a known concentration. In one embodiment, a second temperature controlled zone is provided downstream, and at a lower temperature than the first zone, to ensure saturation of the carrier gas passing through the second zone.

13 Claims, 2 Drawing Sheets

5,789,258

1
METHOD FOR GENERATING VAPOR STREAMS

This invention was made with Government support. The Government has certain rights in the invention.

BACKGROUND OF THE INVENTION

This invention relates generally to the generation of chemical vapors and, more particularly, to methods and apparatus for the generation of chemical vapors for delivery to vapor detection devices such as for calibration purposes and to other types of systems which utilize such vapors.

Chemical vapor detectors have been developed for uses such as the detection of hidden bombs and other concealed explosives. One type of vapor detector operates by extracting air samples from an area being monitored, concentrating any chemical vapors present in the air sample, and then analyzing the concentrated vapors to determine whether a particular chemical vapor, such as an explosives vapor, is present. In order to ensure that the presence of explosives and other chemicals can be detected with confidence and reliability, periodic testing and calibration of such vapor detectors is necessary.

Testing and calibration of vapor detectors can be accomplished with the use of vapor generators of the type that pass a carrier gas over the solid or liquid chemical to deliver a stream of volatilized vapors to the detector. An example of such a generator is disclosed in Pella, P. A., *Analytical Chemistry*, 48:1632–1637 (1976). Because the rate of vaporization of the chemical varies considerably in response to temperature variations and other conditions, it has heretofore been difficult to generate a vapor stream which is both at a constant rate and of a preselected concentration using conventional vapor generators.

As new vapor detection systems are developed, a need has arisen for some comparison method to gauge the performance and sensitivity of such systems with reference to existing detection systems. Although current vapor generators can generate known vapor concentrations approaching one part per billion (ppb), vapor generators with even greater sensitivity and reliability are required to provide a reference vapor concentration for use in the comparison of vapor detectors.

SUMMARY OF THE INVENTION

It is an object of this invention to provide a method and apparatus for generating a chemical vapor stream having a preselected vapor concentration suitable for use in calibrating vapor detectors and/or providing a reference for use in evaluating the performance of different vapor detectors.

It is also an object of this invention to provide a vapor generator which may be readily transported for onsite testing of vapor detection systems so that the calibration of the vapor detector is not compromised by transporting it from the testing site.

It is another object of this invention to provide a vapor generator which minimizes adsorption losses of the vapor within the generator so that a consistent and reproducible vapor concentration may be reliably generated.

It is a further object of this invention to provide a vapor generator which precisely controls the temperature in the vaporization zone so that an equilibrium vapor concentration may be consistently produced.

It is a still further object of this invention to provide a vapor generator with a dual temperature zone to ensure that a saturated vapor stream is produced over a range of output flow rates.

2

To accomplish these and other related objects of the invention, methods and apparatus are provided for generating a vapor stream of known and reproducible concentration. The apparatus for generating the vapor stream comprises a column for containing a chemical associated with a substrate, an inlet line coupled with the column for introducing a carrier gas into the column for passage through the column to mix with vapors of the chemical, and a temperature controlled zone within the column for producing a known vapor concentration within the column zone. The column may include a second temperature controlled zone downstream from the first zone. The second zone is controllable to a lower temperature than the first zone to ensure that the vapor equilibrium in the second zone is at saturation point for the vapor. The apparatus may also include a mixing chamber for diluting the vapor stream to produce a range of preselected vapor concentrations. The method for generating the vapor stream comprises the steps of providing a column containing a chemical and vapors from the chemical, controlling the temperature within a zone of the column upstream from the column outlet to maintain a constant vapor concentration in the zone, and passing a carrier gas through the zone to mix with the vapor and form the vapor stream. The method may include the additional independent steps of controlling the temperature in a zone downstream from the first zone to a lower temperature than the first zone to provide an oversaturated vapor concentration in the second zone, and diluting the vapor stream to provide additional vapor concentrations.

BRIEF DESCRIPTION OF THE DRAWINGS

In the accompanying drawings which form a part of the specification and are to be read in conjunction therewith.

DESCRIPTION OF THE PREFERRED EMBODIMENTS

Figure 1:
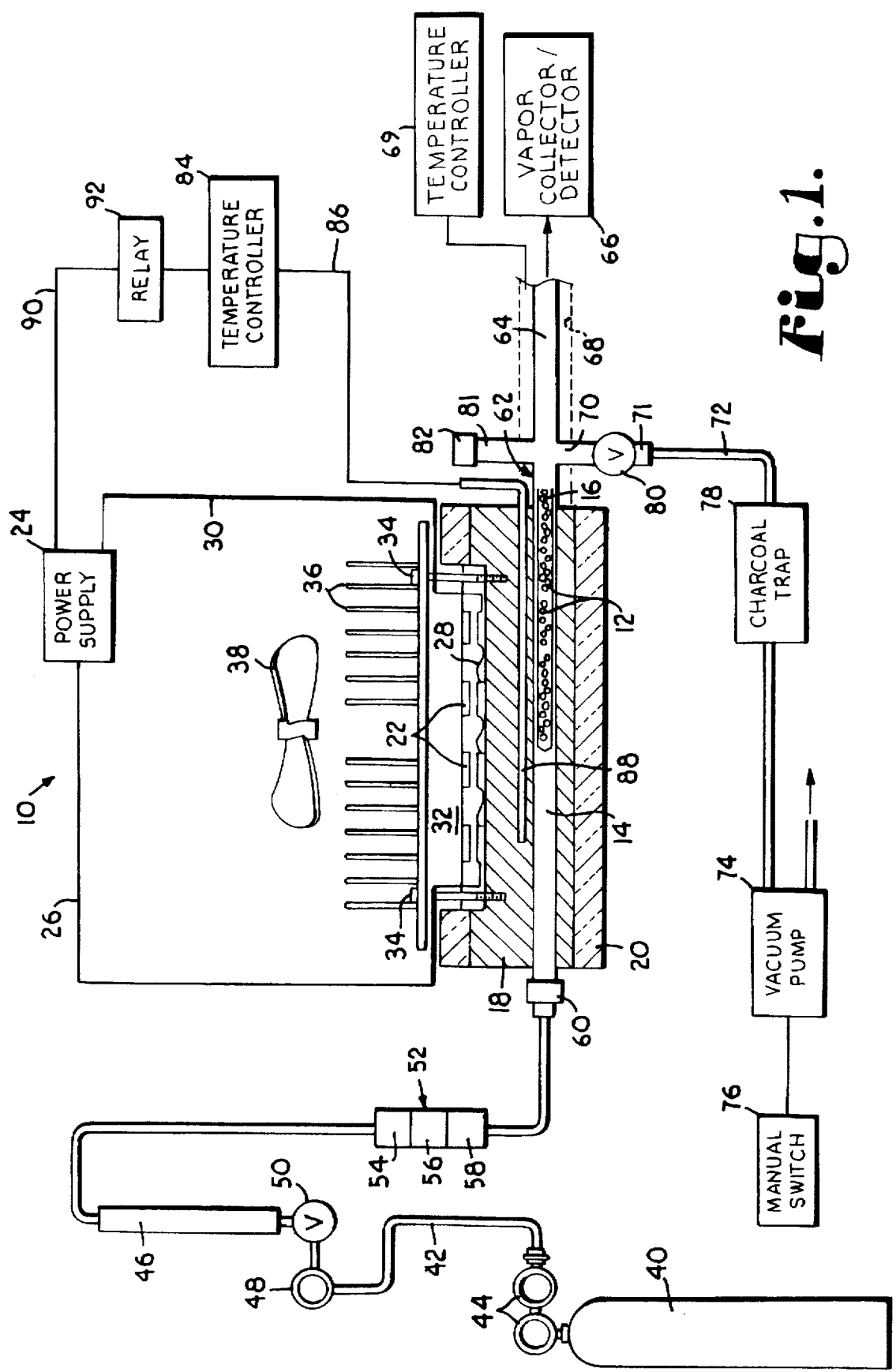
FIG. 1 is a side elevational view, shown somewhat schematically, of one embodiment of a chemical vapor generator of the present invention with a portion broken away and others shown in vertical section for purpose of illustration.

Referring now to the drawings in greater detail and initially to FIG. 1, one embodiment of a vapor generator of the present invention is represented broadly by the numeral 10. The vapor generator 10 is particularly suited for generating a continuous stream of a vapor, such as an explosives vapor, at a preselected concentration for use in calibrating a vapor detection system.

The vapor generator 10 includes a plurality of porous glass beads 12, coated with a liquid or solid chemical substance, which may be volatilized to produce the desired vapor. The chemical is coated on the beads and within the pores of the beads in a suitable fashion such as by mixing the chemical with a solvent, adding the beads to the mixture, and then heating or otherwise drying the beads to drive off the solvent. The concentration of the chemical associated with the beads may be varied depending upon the chemical used. A concentration of approximately 10%, on a weight basis, has been found suitable when explosives such as 2,4,6-trinitrotoluene (better known as TNT) are used. Similar concentrations may be used for other chemicals. Beads having a mesh size of 35 to 60 obtained from Sigma Chemical Co. were utilized in the development of the generator 10, but other carriers or substrates which provide a large surface area for the chemical may be utilized. Explosives such as TNT were used as model chemicals in the development of the generator, but it is to be understood that the generator has utility for producing vapors of other suitable chemicals.

The glass beads 12 and the associated chemical are packed within an elongated cylindrical tube or column 14. Although the dimensions of the column may be varied as desired, a column six inches in length with a ¼ inch outer diameter and a 4 mm inner diameter has been found to be particularly suitable and readily portable. Column 14 preferably comprises a glass tubing which has been silanized, such as by treatment with a solution of dimethyl dichlorosilane, followed by rinsing with toluene and subsequent drying. All other components of the generator 10 which come into contact with the vapor generated are also preferably silanized glass to reduce adsorption of the vapor onto the component surfaces. The glass beads 12 are maintained within column 14 by Teflon wool plugs 16 which are placed within the column at both the inlet and outlet thereof.

The column 14 which houses beads 12 is enclosed within a cylindrical solid aluminum housing 18 which itself is enclosed within a layer of insulation 20 to facilitate control of the temperature within the column. The aluminum housing 18 includes a flat outer surface on which are mounted a plurality of bimetallic thermoelectric coolers 22 which transfer heat from one surface to another upon directional application of electric current. Heat transfer of this type is based upon the principle known as the Peltier effect. The coolers 22 operate to control the temperature of column 14 to within 0.1° C. so that the vapor concentrations which are generated within the column may be precisely controlled. Constant voltage and current are directionally supplied to the coolers from a power supply 24 through suitable conductors or leads 26, 28 and 30. Power supply 24 may comprise a battery or other suitable power source.

A heat sink 32 is in contact with the side of coolers 22 opposite from the side which is in contact with housing 18. The heat sink 32 is secured to aluminum housing 18 by bolts 34. A plurality of heat transfer fins 36 extend from the heat sink and a cooling fan 38 is provided to direct airflow across the fins 36 to dissipate heat from the heat sink.

A carrier gas, preferably an inert gas such as prepurified nitrogen, is delivered to column 14 from tank 40 through flow line 42. The flow of nitrogen from tank 40 is controlled to a pressure of 15 psi or other desired pressure by a two-stage regulator 44 provided in line 42. The flow rate within line 42 is measured by a rotameter 46 which is located upstream from the column 14. A pressure gauge 48 and needle valve 50 are placed in line 42 to allow precise regulation of the flow of nitrogen to the column 14. The needle valve is positioned upstream from the column 14 to eliminate vapor losses resulting from the vapors flowing through and interacting with the valve orifice.

Residual impurities such as oxygen, water, and hydrocarbons are removed from the nitrogen before entry into column 14 by a cleanup column 52 which contains a silica gel zone 54, a molecular sieve zone 56, and an activated charcoal zone 58.

A suitable fitting 60 connects flow line 42 with the glass column 14 to permit the purified nitrogen to be directed through the column. As the nitrogen flows through the glass bead packing within the column, it becomes saturated with vapors from the chemical associated with the glass beads 12. A downstream end 62 of the column provides an outlet for the resulting nitrogen and vapor mixture and a glass transfer line 64 is connected with the outlet for directing the mixture to a vapor detector or sampler 66. The transfer line 64 is preferably silanized and maintained at an elevated temperature such as by wrapping with heat tape 68. A temperature controller 69 is provided to monitor the temperature of the transfer line 64 and to regulate the heating supplied by heat tape 68.

A cross connector 70 is provided between the column outlet 62 and glass transfer line 64 to permit the nitrogen and vapor flow to be shunted away from the transfer line by application of a vacuum to the connector. A leg 71 of the connector is coupled with a shunt line 72 which leads to a vacuum pump 74. A manual switch 76 is provided for activating the vacuum pump when shunting of the nitrogen and vapor from the transfer line 64 is desired. A charcoal trap 78 is provided within line 72 to remove the vapors from the nitrogen gas flowing through line 72. A valve 80 placed in the connector leg 71 controls fluid flow within line 72.

The other leg 81 of connector 70 provides a port which may be used for inserting a tube to sample the nitrogen and vapor stream. A plug 82 caps the connector leg 81 when the port is not in use.

Precise regulation of the temperature within column 14 is critical to the operation of generator 10 and production of the desired vapor concentrations. Temperature monitoring is provided by a temperature controller 84 connected by lead 86 to a platinum resistance temperature detector probe 88 inserted into aluminum housing 18. The temperature probe 88 has a sensitivity to detect temperature changes of at least ±0.1° C. and extends along and is closely spaced from column 14 within housing 18. Temperature controller 84 is connected by lead 90 to power supply 24 to activate thermal electric coolers 22 in a manner to provide the necessary temperature control. A relay 92 is provided in the lead 90, connecting the temperature controller with the power supply.

In operation, the vapor generator 10 maintains a predetermined temperature in column 14 to provide a preselected vapor concentration, preferably a saturated concentration, within the column. Because the vapor pressure of the chemical maintained within the column 14 varies exponentially in relation to temperature changes within the column, precise control of the column temperature is required to ensure that the vapor concentrations produced remain consistent. Temperature probe 88 allows constant monitoring of the column temperature to within at least ±0.1° C. As temperature changes are detected, temperature controller 84 activates power supply 24 to supply coolers 22 with the directional current necessary to return the column to the preselected temperature.

The temperature within column 14 is selected in conjunction with the flow rate of purified nitrogen through the column to ensure that vapor saturation is maintained within the column as the nitrogen gas passes therethrough. Temperature and flow rate ranges, which permit vapor saturation within the column for various chemicals, may be readily determined by those skilled in the art.

The velocity of the nitrogen carrier gas entering the column 14 is controlled upstream from the column by needle valve 50. The needle valve may be adjusted to meter the nitrogen flow to the rate desired, preferably within the range of 5 to 200 mL/min., with the rotameter 46 providing a reading of the flow rate. Positioning of the needle valve 50 upstream from the column prevents the vapor losses which would otherwise result if the flow rate were controlled downstream from the column and the vapors passed through and interacted with the valve.

The vapor concentration within column 14 is also affected by the surface area of the chemical within the column. The use of glass beads 12 as a carrier for the chemical provides a large surface area of approximately 26.1 m²/g but requires only a relatively small quantity of chemical. This large surface area contributes to the reproducibility of a desired vapor concentration as small variations in the surface area result in negligible or no changes in the vapor concentration. The desired vapor concentration can then be reliably reproduced even after repeated uses of the generator 10 without requiring recharging of the chemical. The ability to coat a large bead surface area with only a small quantity of chemical is also particularly important when explosive or otherwise hazardous chemicals are associated with beads 12.

The chemical vapors within column 14 mix with the nitrogen gas flowing through the column to form the saturated vapor stream mixture. The mixture exiting the column is directed through glass transfer line 64 to the intake of vapor sampler or detector 66 for calibration or other purposes. Vapor losses resulting from adsorption of the vapor onto component surfaces as it is directed to detector 66 are kept to a minimum by heating the glass transfer line 64 with heat tape 68. Heating of the transfer line to reduce adsorption losses must also be balanced against the risk of vapor loss resulting from thermal degradation of the vapor. It has been found that maintaining the transfer line within the range of approximately 100° to 150° C. provides satisfactory results when the vapor mixture comprises nitrogen and TNT vapors.

The surface area of transfer line 64 is advantageously kept to a minimum to reduce the available area onto which the vapor can adsorb. Adsorption losses which would result from placement of metering or other valves downstream from the column outlet are also avoided in generator 10 by placement of valve 50 and other flow control components upstream from column 14.

When the vapor mixture stream flowing from the column 14 is to be interrupted, such as between calibrations of the vapor detector 66, manual switch 76 is engaged to activate the vacuum pump 74 and shunt valve 80 is opened. The vacuum produced by pump 74 draws the vapor stream through line 72 and charcoal trap 78 where the chemical vapor is trapped, the nitrogen then being expelled from the discharge of the vacuum pump. This vacuum shunting of the vapor stream allows the vapor stream flow through the transfer line 64 to be controlled without the positioning of valves or similar directional control devices directly in the transfer line. Vapor adsorption losses which would otherwise result from such valves are avoided, thereby permitting greater accuracy and control over the vapor concentration in the vapor stream. The port for obtaining vapor samples from the column outlet is likewise removed by connector leg 81 from the flow path of the vapor stream to prevent interaction of the port with the vapor. It can thus be seen that the vapor mixture produced by the column is transferred directly to the intake of the vapor detector 66 without passing through valves or other obstructions which would alter the vapor concentration.

Preselected vapor concentrations can be reliably and reproducibly achieved with generator 10 by the described method of controlling the temperature within column 14 to within ±0.1° C., utilizing glass beads 12 to obtain a large surface area substrate for the chemical, and directing the vapor mixture directly to the detector 66 with a minimum of vapor loss that would result from adsorption onto contact surfaces. Transport of generator 10 is facilitated by the use of thermoelectric coolers 22 which are mounted directly on the housing 18 to provide the desired column temperature. Because of its portable construction, the vapor generator 10 can be taken to the location where the vapor detector 66 is installed to calibrate or otherwise challenge the detector. By testing the vapor detector 66 in place, a more reliable indication of the sensitivity of the detector may be provided and compromise of the detector calibration as a result of transportation of the detector is avoided.

Figure 2:
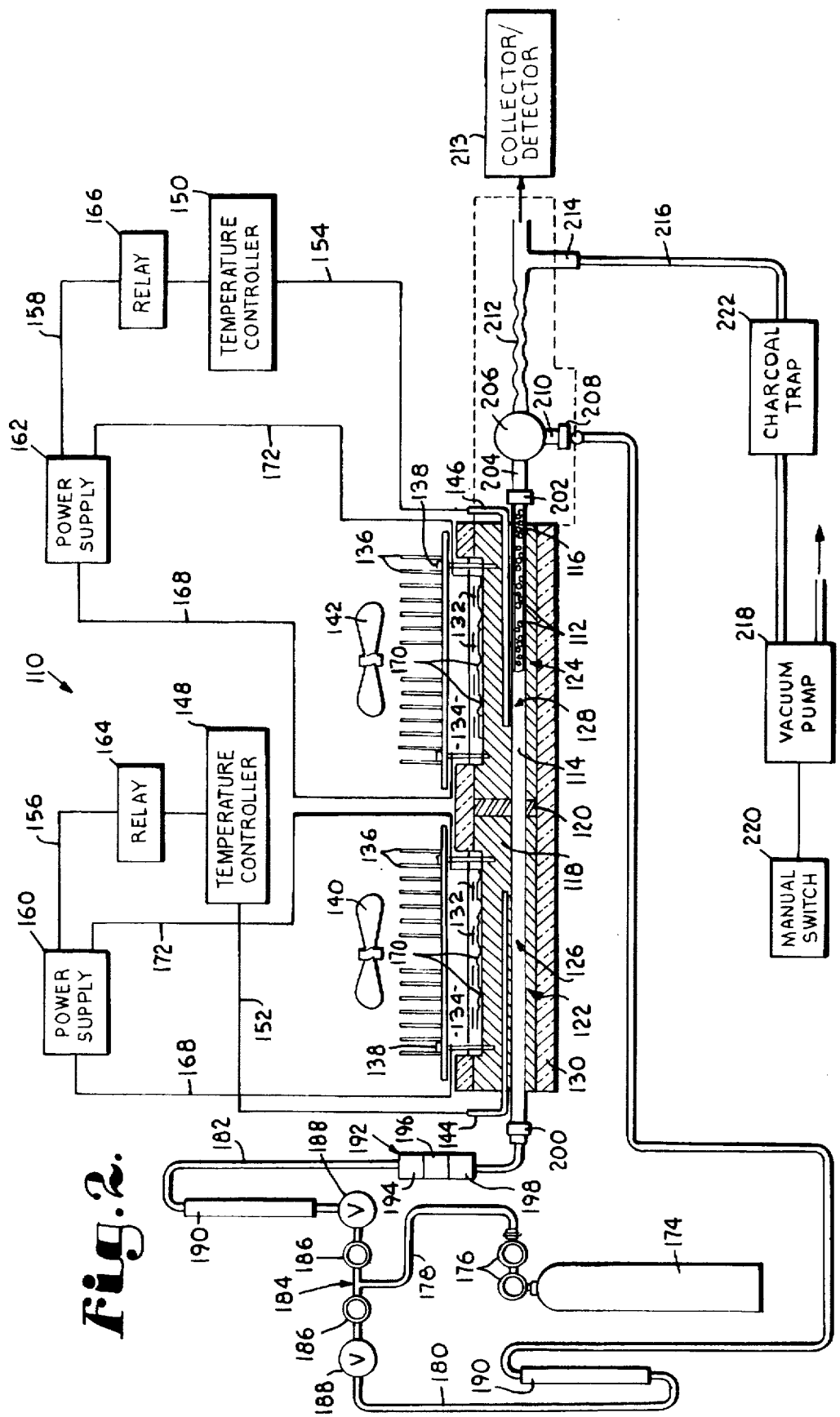
FIG. 2 is a side elevational view of a second embodiment, shown somewhat schematically, of a chemical vapor generator of the present invention with a portion broken away and others shown in vertical section for purpose of illustration.

Turning now to FIG. 2, an alternate embodiment of a vapor generator of the present invention is represented by the numeral 110. Vapor generator 110 is characterized by dual temperature zones and a dilution feature which permit variable flow rates and concentrations to be accurately reproduced.

Vapor generator 110 includes a plurality of glass beads 112 of the type previously described packed into and along a substantial length of a silanized glass column 114, also similar to that previously described but having a length of twelve inches. Teflon wool plugs 116 are provided at both ends of the column.

An elongated aluminum housing 118 surrounds the column 114 and includes a centrally positioned foam gasket 120 to reduce thermal transfer between the resulting upstream and downstream housing segments 122 and 124. The foam gasket 120 also serves to create first and second column zones 126 and 128 which may be regulated at different temperatures.

An insulation layer 130 surrounds the aluminum housing to facilitate control of the temperature within column 114. Temperature monitoring and control are effected in the same manner previously described. Both housing segments 122 and 124 include identical flat surfaces on which are mounted thermoelectric coolers 132 of the type previously described. Heat sinks 134 are provided in contact with coolers 132 in both housing segments 122 and 124 and include a plurality of heat exchange fins 136. The heat sinks are secured to their associated housing segments by bolts 138. Independently operable cooling fans 140 and 142 are provided for facilitating heat transfer from fins 136.

Suitable temperature detector probes 144 and 146 are provided within both housing segments 122 and 124 and are connected to temperature controller units 148 and 150 by leads 152 and 154 respectively. Temperature probe 146 associated with downstream housing segment 124 is preferably a platinum resistance type probe suitable for detecting temperature variations of ±0.1° C. Temperature probe 144 associated with upstream housing segment 122 may comprise various suitable thermocouple probes capable of detecting temperature variations of ±1° C. Both temperature controllers 148 and 150 are independently connected by leads 156 and 158 to a respective power supply 160 and 162. Suitable relays 164 and 166 are provided in leads 156 and 158 for controlling activation of the associated power supplies. The power supplies 160 and 162 provide constant voltage and current to the thermal electric coolers 132 which are wired to the respective power supplies by leads 168, 170, and 172.

A carrier gas such as nitrogen is directed to the column from a tank 174 provided with a two stage regulator 176 such as previously described. A flow line 178 leading from tank 174 divides into a dilution line 180 and a flow line 182 at a T-junction 184. Both lines 180 and 182 are provided with a pressure gauge 186, a needle valve 188, and a rotameter 190 of the type previously described. Flow line 182 also includes a cleanup column 192 having a silica gel zone 194, a molecular sieve zone 196, and an activated charcoal zone 198 for further purifying the nitrogen before it is introduced into column 114. A suitable connector 200 connects flow line 182 to the inlet of packed column 114. Another connector 202 couples the outlet of column 114 with a short, glass tube 204 that leads to a mixing chamber 206.

The dilution line 180 that branches from the nitrogen tank flow line 178 is also connected at its downstream end to the mixing chamber 206 by a connector 208 and a glass tube 210. A glass transfer line 212 leads from the mixing chamber 206 to a collector or detector 213 and is dimpled to cause turbulence within the vapor stream to ensure complete mixing of the carrier gas and vapor. Heat tape is wrapped around the components 202–212 to reduce adsorption losses in the manner previously described.

A connector leg 214 branches from the transfer line 212 and is coupled with flow line 216 to shunt the vapor stream from the discharge end of the transfer line. A vacuum pump 218 operated by manual switch 220 is connected to flow line 216 to provide the necessary vacuum to draw the vapor stream through the flow line. An activated charcoal trap 222 in the flow line operates to remove the chemical vapors from the vapor stream so that only the carrier gas is vented by the vacuum pump. Sampling ports (not shown) of the type previously described may also be placed in transfer line 212.

Vapor generator 110 operates in a manner similar to vapor generator 10 previously described by passing a nitrogen carrier gas through column 114 to mix with vapors from the chemical contained therein to produce a vapor stream of a preselected concentration. The presence of two temperature controlled zones 126 and 128 in generator 110, however, ensures that the vapor concentration is at saturation even at nitrogen flow rates greater than those at which saturation will occur in generator 10.

The upstream zone 126 of column 114 is maintained at a temperature chosen to produce vapor saturation, or near saturation, in zone 126 at the nitrogen flow rate(s) selected. The downstream zone 128 is maintained at a lower temperature than zone 126 to preferably cause oversaturation and condensation of a portion of the vapor stream as it passes through the downstream zone, thereby ensuring that the vapor stream exiting the column 114 is at saturation. The column 114 is also of a length which provides sufficient residence time for the carrier gas within the column to mix with the chemical vapors. The temperature differential between the two zones is selected in conjunction with the flow rate, vapor pressure of the chemical, and other relevant variables, but usually is with in the range of 3° to 5° C.

Temperatures within zone 126 need only be maintained to within ±1° C., but temperatures within zone 128 are preferably maintained to within ±0.1° C. to ensure precise control over the generated vapor concentration. Temperature monitoring and control within the zones is accomplished in the manner previously described with reference to generator 10.

Generator 110 also provides for dilution of the vapor stream exiting column 114 so that a range of vapor concentrations may be provided. The diluent preferably comprises purified nitrogen gas taken from the same tank as the nitrogen carrier gas to prevent any interactions which might affect vapor concentration. The diluent nitrogen is delivered through line 180 to the mixing chamber 206 where it mixes with the vapor stream exiting from column 114 to provide a diluted vapor concentration in the resulting mixture. The pressure in line 180 is typically several psi lower than in line 182 to ensure a constant flow rate of the carrier gas through column 114. The flow rate of diluent gas delivered to chamber 206 is controlled by valve 186 located in line 180. Typically, the flow rate of the diluent nitrogen is within the range of 100 to 5000 mL/min. while the flow rate of the carrier nitrogen is between 10 and 150 mL/min.

The vapor mixture exiting from chamber 206 is further mixed in dimpled transfer line 212 and is delivered to the vapor detector 213. When interruption of the vapor mixture delivery is desired, the vacuum pump 218 is simply activated to shunt the mixture through line 216 in the manner previously described.

The precise vapor concentration control provided by generator 110 at varying flow rates makes the generator 110 particularly suited for providing vapor streams of drugs, pollutants, toxins, and explosives for use in developing and evaluating new detection technologies.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without department from the scope thereof, it is to be understood that all matter herein set forth or shown in the accompanying drawings is to be interpreted as illustrative and not in a limiting sense.

Having thus described the invention, what is claimed is:

1. A method of generating a stream containing a preselected concentration of vapor of a chemical for use in a vapor detector, said method comprising the steps of:
   providing a column;
   providing said chemical on a substrate in the column;
   controlling the temperature within a zone of the column to within approximately 0.1° C. of a preselected temperature to provide a concentration of said vapor within the zone;
   passing a carrier gas at a controlled rate through the column to mix with the vapor and form said stream containing the preselected concentration of vapor; and
   directing the stream from the column to the vapor detector.

2. The method of claim 1, wherein the step of providing the chemical on a substrate includes the step of providing said chemical on a plurality of glass beads and packing the beads within the column.

3. The method of claim 1, including the step of controlling the temperature in a second zone downstream from said first mentioned zone, said second zone being controlled to a lower temperature than said first zone to provide an oversaturation of vapor in said second zone as said carrier gas passes through the second zone.

4. The method of claim 1, including the step of controlling the temperature in the zone to provide a saturation concentration of vapor in the zone as the carrier gas passes through the zone.

5. The method of claim 1, including the step of shunting selectively the stream away from the vapor detector by selective application of a vacuum to the stream.

6. The method of claim 1, including the step of controlling the flow rate of the carrier gas at a location upstream from the column.

7. The method of claim 1, including the step of diluting the stream to change the vapor concentration within the stream prior to said step of directing the stream to the vapor detector.

8. The method of claim 7, wherein the step of diluting the stream comprises the step of diluting the stream with an inert gas comprising the carrier gas.

9. A method of generating a stream containing a preselected concentration of vapor of a chemical for use in a vapor detector, said method comprising the steps of:

providing a column;

providing said chemical on a substrate in the column;

passing a carrier gas at a controlled rate through the column to mix with vapor from the chemical and form said stream; and controlling the temperature within a zone of the column to provide a saturation concentration of said vapor in the stream within the zone; and directing the stream from the column to the vapor detector.

10. The method of claim 9, including the step of providing said chemical on a plurality of glass beads and packing the beads within the column.

11. The method of claim 9, including the step of controlling the temperature to within approximately 0.1° C. of a preselected temperature.

12. The method of claim 9, including the step of controlling the temperature in a second zone downstream from the first mentioned zone, said second zone being controlled to a lower temperature than said first zone to provide an oversaturation of vapor in said second zone as said carrier gas passes through the second zone.

13. The method of claim 9, including the step of diluting the stream to change the vapor concentration within the stream prior to said step of directing the stream to the vapor detector.

* * * * *